(12) United States Patent
Doty et al.

(10) Patent No.: US 8,001,968 B2
(45) Date of Patent: Aug. 23, 2011

(54) APPARATUS FOR DELIVERING AND/OR SCAVENGING GAS IN THE NOSE/MOUTH AREA OF A PATIENT

(76) Inventors: Robert H. Doty, Richfield, OH (US);
Scott B. Doty, Philadelphia, PA (US)

( * ) Notice: Subject to any disclaimer, the term of this patent is extended or adjusted under 35 U.S.C. 154(b) by 1079 days.

(21) Appl. No.: 11/746,069

(22) Filed: May 9, 2007

(65) Prior Publication Data

US 2008/0276941 A1    Nov. 13, 2008

(51) Int. Cl.
*A61M 16/06*    (2006.01)
(52) U.S. Cl. ......... 128/205.27; 128/207.13; 128/207.18; 128/204.18
(58) Field of Classification Search ............ 128/206.11, 128/206.24, 206.28, 207.13, 207.18, 910; 285/188, 420
See application file for complete search history.

(56) References Cited

U.S. PATENT DOCUMENTS

| | | | |
|---|---|---|---|
| 3,537,447 A | 11/1970 | Gauthier et al. | |
| 3,799,164 A | 3/1974 | Rollins | |
| 4,015,598 A | 4/1977 | Brown | |
| 4,151,843 A | 5/1979 | Brekke et al. | |
| 4,219,020 A | 8/1980 | Czajka | |
| 4,248,218 A | 2/1981 | Fischer | |
| 4,265,239 A | 5/1981 | Fischer, Jr. et al. | |
| 4,312,339 A | 1/1982 | Thompson, Sr. | |
| 4,354,488 A * | 10/1982 | Bartos ................. | 128/205.25 |
| 4,446,861 A | 5/1984 | Tada | |
| 4,523,590 A * | 6/1985 | Roth et al. ................. | 128/831 |
| 4,538,605 A | 9/1985 | Gedeon et al. | |
| 4,770,169 A | 9/1988 | Schmoegner et al. | |
| 4,865,049 A | 9/1989 | Gatti | |
| 4,889,490 A | 12/1989 | Jenkinson | |
| 4,895,172 A | 1/1990 | Lindkvist | |
| 4,987,894 A | 1/1991 | Knight | |
| 5,018,519 A | 5/1991 | Brown | |
| 5,033,464 A | 7/1991 | Dicastilho | |
| 5,046,491 A * | 9/1991 | Derrick ................. | 128/200.24 |
| 5,195,512 A | 3/1993 | Rosso | |
| 5,370,110 A | 12/1994 | Corn | |
| 5,419,317 A | 5/1995 | Blasdell et al. | |
| 5,513,632 A | 5/1996 | Nepon et al. | |
| 5,636,627 A | 6/1997 | Rochester | |

(Continued)

OTHER PUBLICATIONS

King Systems Corporation, Expanding into New Markets, King LT-D EMS Kit, http://www.kingsystems.com/Default.aspx?tabid=185.

(Continued)

*Primary Examiner* — Justine R Yu
*Assistant Examiner* — Valerie Skorupa
(74) *Attorney, Agent, or Firm* — D.A. Stauffer Patent Services (57) ABSTRACT

Apparatus for delivering and scavenging anesthesia gas for a patient. A lower elongate piece forming a nose cannula for delivering gas, is removably secured generally parallel and immediately adjacent to an upper elongate piece for scavenging gas. The upper piece extends over a lower portion of the patient's nose, and has a plurality of openings disposed on a lower surface thereof, directed downward towards the patient's mouth. Both ends of the lower and upper pieces are provided with barbs for receiving corresponding supply and exhaust hoses at one end. Barbs at the other end are sealed by an end cap. A strap secures the apparatus on the patient's head. Thus the apparatus can be advantageously used with hoses on only one side of the face, thereby allowing the user to work with minimal obstruction on the opposite side of the face.

17 Claims, 4 Drawing Sheets

U.S. PATENT DOCUMENTS

| | | | |
|---|---|---|---|
| 5,715,813 A | 2/1998 | Guevrekian | |
| 6,135,109 A | 10/2000 | Blasdell et al. | |
| 6,263,874 B1 | 7/2001 | LeDez et al. | |
| 6,308,707 B1 | 10/2001 | Lu | |
| 6,718,981 B2 | 4/2004 | Cardarelli | |
| 6,736,140 B1 | 5/2004 | Baczkowski | |
| 2001/0035185 A1* | 11/2001 | Christopher | 128/204.17 |
| 2002/0017300 A1* | 2/2002 | Hickle et al. | 128/204.22 |
| 2004/0020493 A1* | 2/2004 | Wood | 128/207.18 |
| 2006/0032509 A1 | 2/2006 | Milles | |
| 2006/0076013 A1 | 4/2006 | Berg | |
| 2006/0130840 A1* | 6/2006 | Porat et al. | 128/206.11 |

OTHER PUBLICATIONS

Airgas Puritan Medical, Safe Sedate Dental Nasal Mask brochure, MCM-062, @2005 Airgas, Inc.

Anaequip, http://www.anaequip.com/econo.htm#dental (especially p. 5 of 6 in the printed web page).

* cited by examiner

APPARATUS FOR DELIVERING AND/OR SCAVENGING GAS IN THE NOSE/MOUTH AREA OF A PATIENT

TECHNICAL FIELD OF THE INVENTION

The present invention relates to devices for administering inhalation anesthesia gas to patients, particularly in a dental environment, and exhausting/ventilating waste gases and/or anesthesia gases which may be leaked from the administration device and/or exhaled by a patient either through his mouth or nose. As defined herein, the term "gas" may include any gaseous material plus any gas-entrained or aerosol liquids, such as, for example, spattered or sprayed drill-cooling water mixed with saliva.

BACKGROUND OF THE INVENTION

Anesthesia has traditionally meant the condition of having the perception of pain and other sensations blocked. This allows patients to undergo surgery and other procedures without the distress and pain they would otherwise experience.

The anesthetic qualities of nitrous oxide (isolated in 1773 by Joseph Priestley) were discovered by the British chemist Humphrey Davy about 1799 when he was an assistant to Thomas Beddoes, and reported in a paper in 1800. But initially the medical uses of this so-called "laughing gas" were limited—its main role was in entertainment. It was used on 30 Sep. 1846 for painless tooth extraction upon patient Eben Frost by American dentist William Thomas Green Morton.

Forms of dental anesthesia are similar to general medical anesthesia except for the use of nitrous oxide, relatively uncommon outside of the dental field in the U.S. Nitrous oxide (N2O), also known as "laughing gas", binds to the hemoglobin in the lungs, where it travels to the brain, leaving a disassociated and euphoric feeling for most patients. N2O is typically used in conjunction with Procaine.

In *Policy on Minimizing Occupational Health Hazards Associated With Nitrous Oxide* The American Academy of Pediatric Dentistry (AAPD) recommends that exposure to ambient nitrous oxide be minimized to reduce occupational health hazards associated with nitrous oxide.

Collection of ambient nitrous oxide involves 2 separate mechanisms. The first, the scavenging system, is part of the nitrous oxide delivery system. It begins at the nitrous oxide tanks and terminates at the expiratory valve in the mask. Canadian studies in hospital settings have shown that frequent and regular inspection and maintenance of the nitrous oxide delivery system, together with the use of a scavenging system, can reduce ambient nitrous oxide significantly.

Another reason for providing gas scavenging apparatus is to scavenge aerosols and splatter (air-entrained liquids) which are believed to spread infections among dental personnel.

In the dental environment, patient behaviors such as talking, crying, and moving have been shown to result in significant increases in baseline ambient nitrous oxide levels despite the use of the mask-type scavenging systems. By using a well-fitted mask and an appropriate amount of suction via the scavenging system, the increased pressure on the patient's face by the mask will reduce leakage.

NIOSH (National Institute for Occupational Safety and Health) has recommended an oral evacuation rate of 45 L/min for maximizing scavenger effectiveness. However, scavenging at this rate has been shown to reduce the level of psychosedation achieved with nitrous oxide inhalation.

The second mechanism, the "exhaust system", collects escaped nitrous oxide and includes two entities. First, an appropriate non-recirculating ventilation system is recommended by NIOSH to provide continuous rapid air exchange. It is important to vent waste gases outside of the building and away from fresh air intakes.

Second, a high-volume aspirator, placed near or within 20 cm of the patient's mouth, has been shown to reduce significantly ambient nitrous oxide levels in the dental environment.

Diligent use of these two mechanisms in the pediatric dental environment has allowed for the reduction of ambient nitrous oxide to the levels recommended by NIOSH.

The AAPD recommends that dentists and dental auxiliaries minimize their exposure to nitrous oxide by maintaining the lowest practical levels in the dental environment. Adherence to the recommendations below can help minimize occupational exposure to nitrous oxide.

1. Scavenging systems must be used when nitrous oxide is employed.
2. Exhaust systems that adequately vent scavenged air and gases to the outside of the building and away from fresh air intake vents should be employed.
3. Careful, regular surveillance and maintenance of the nitrous oxide/oxygen delivery equipment must be practiced.
4. Mask size should be such as to ensure proper fit for each patient.
5. Nitrous oxide discharge from the oral cavity of the patient should be minimized during dental procedures.

Various patents describe method and apparatus for administering anesthesia gas and scavenging waste gases, as exemplified by the following.

U.S. Pat. No. 4,151,843 ("843 patent") discloses apparatus for administration of a gas to a human and the exhausting thereof. An apparatus for administration of a gas to a human and the exhausting thereof including a gas flow control connected to one end of a gas administering device which has on the other end protrusions for sealing engagement with nostrils of the nose. A gas supply conduit is connected to the gas flow control and a gas exhaust conduit is connected to the gas flow control, the gas flow control causes an intake of gas through the supply conduit and said gas administering device and out said protrusions thereon upon inhalation of a user of the apparatus. The gas flow control causes the exhausting of exhaust gas from said gas administering device through said gas flow control and out said gas exhaust conduit to a gas collector upon expiration of the user of the apparatus. The gas flow control causes the flow of fresh gas through a supply conduit to be blocked during user expiration.

In the 843 patent, a fairly small nose cap seals against nostrils and channels gas into the nostrils during inhalation and vacuums exhalation from the nostrils (only) through the same nose seal. Also exhausts gas that may leak from seal against nostrils. Hoses pass around both sides of head but elevated above eye level. The device only scavenges from inside the mask (the patient's nose), not the mouth. The routing of hoses on both sides of the mask may impair access by the doctor.

U.S. Pat. No. 5,513,632 ("632 patent") discloses ventilation of medical gases. A downdraft system is used for withdrawing and collecting medical gases, fumes, mists and particulates from the vicinity of a patient's face. Two intakes are located on respective sides of the patient's face, at the cheeks. The intakes extend from temple to chin. They are connected through a ducting system to a source of vacuum for collecting the medical gases. The ducting system is configured to allow the adjustment of the intake positions. The intakes create a flow of air across the patient's face from above the nose to below the mouth so that gases leaking during administration of gases or exhaled by the patient, and fumes, mists or low velocity particulates generated, for example, in orthodontic procedures are captured in the flow across the patient's face into the intakes. This leaves the patient's mouth and nose fully exposed and unobstructed by the gas evacuation apparatus so that the administration of gases, dental treatments and any other procedures requiring access to the mouth and nose area may be carried out.

In the 632 patent, scavenging intakes are provided in the facial area without a nose-enclosing mask. This device does not supply an anesthetic gas to the patient.

U.S. Pat. No. 4,770,169 ("169 patent") discloses an anesthetic scavenging face mask having a scavenging channel running along the perimeter of the mask. The mask is provided with an anesthetic gas inlet and a vacuum outlet. The scavenging channel is connected to the vacuum outlet.

In the 169 patent, only gases exhaled from the patient's nose are exhausted, and hoses coming out of both sides of the mask may impair access to the patient's mouth by a dentist.

U.S. Pat. No. 4,248,218 ("218 patent") discloses a scavenging mask apparatus for administering gas to a patient, the apparatus comprising a nasal cannula for delivering gas to the patient's nostrils, a tube connecting the cannula to a source of gas, a nosepiece adapted to fit over the nose and cannula, and a tube connecting the nosepiece to a source of vacuum. Gas exhaled through the patient's nostrils or escaping from the cannula is scavenged by the air flow in the nosepiece, thereby minimizing loss of gas to the environment. The nosepiece is also provided with a plurality of holes in the underside thereof to scavenge gas exhaled through the patient's mouth.

In the 218 patent, the mask has hoses coming out of both sides, which can impair access to the patient's mouth, by the dentist. Furthermore, the bulky nosepiece may itself impair access to the mouth and vision of the lower quadrant. The holes in the underside are not likely to be very effective since the holes are spread out over a wide area not targeted for creating laminar flow up from the mouth.

U.S. Pat. No. 5,715,813 ("813 patent") discloses capture system for waste anesthetic gas. A waste anesthesia capture system includes exhaust apparatus having a rate of fluid flow of at least five times the rate of anesthesia gas delivered to a patient, the exhaust apparatus having a capacity of at least ten cubic feet per minute. The system further includes an exhaust conduit in fluid-integral communication, at a first opening, with the exhaust apparatus. Also included is a Y-shaped anesthesia gas conduct formed of a flexible memory-retaining material. A cross-section of a base portion of that conduit has an output in fluid-integral communication with a second opening of the exhaust conduit, and each of two branches of the Y-shaped conduit define longitudinal axes, the axes having a selectable separation in the range of nine inches to two feet, and each open end of the branches defining a diameter in the range of 0.5 to 4.0 inches.

In the 813 patent, large round intake tubes for scavenging gas are positioned on either side of the neck. These appear to be bulky, likely to get in the way of a dentist, and difficult to position. A separate mask supplies nitrous oxide. The bulky nosepiece also obstructs vision to the lower quadrant of the mouth.

U.S. Pat. No. 5,636,627 ("627 patent") discloses equipment and method for gas extraction in general anesthesia. Contaminated air in general anesthesia is extracted via a hemispherical hood 1 located closely over the patient. The hood 1, which is of a thin-wall transparent-shell form, is mounted for hand-touch variation of its orientation on an arm 2 which is carried by a telescopic column 3 that allows for height adjustment. The arm 2 extends from a unit 18 that allows the hood 1 to be swung horizontally about the column 3, and gas is drawn from the hood 1 near its open mouth 6 via a low-down port 7 (FIGS. 3 to 5) that is coupled through the arm 2 and column 3 to a fan unit 4. Relief 23 of the bottom margin of the hood 1 may be used to enhance access to the patient, and for maneuverability the column 3 is trolley-mounted or adjustable laterally on a fixed track 35 (FIGS. 9 and 10).

The 627 patent addresses equipment and method for gas extraction in general anesthesia. A lightweight, transparent hemispherical hood is positioned over the patient's face. The hood evacuates escaped/exhaled gases. The hood is quite large, and would appear likely to interfere with any work not done at arm's length. The equipment only scavenges, it does not supply the nitrous oxide to the patient.

U.S. Pat. No. 5,195,512 ("512 patent") discloses apparatus for evacuating excess gases from surgery patient's face. An apparatus for removing introduced or exhaled from the mouth and nose area of a patient via a suction device is disclosed. The apparatus includes a first flexible and hollow cylinder having one closed end and one open end and a plurality of small openings grouped together in a central portion of the first cylinder. The open end is attachable to the suction device. The second flexible and hollow cylinder is attachable to the operating table for supporting the first cylinder. A flexible tube extends through the second cylinder to provide rigidity and malleability to the second cylinder. The first cylinder is coupled to the second cylinder.

In the 512 patent, an exhaust hose is suspended over the nose/mouth area of patient by positionable tubing attached to the exhaust hose. The exhaust hose has several small evacuation holes. The exhaust hose is clamped to an operating table, and the mounting system would appear to be inappropriate for use in dentistry. The device only scavenges, it does not supply nitrous oxide to the patient.

U.S. Pat. No. 3,537,447 ("447 patent") discloses medical shielding structure. A shielding apparatus of a medical operating area which forms a protective air shield between, for example, a dentist and his patient. The shielding apparatus includes a longitudinally extending outlet header having a discharge opening therethrough effective to discharge air in a planar-laminar flow path. Air is supplied to the outlet header by a motor driven blower through a conduit system. An inlet structure is spaced from the outlet header ad receives the shielding airstream. The outlet header and the intake structure are mounted on an articulating support arm. Conduit means lead from the intake structure and I the preferred embodiment, discharge contaminated air passing therethrough to a filter. A portion o the filtered air is recalculated to the outlet header and another portion is exhausted.

The device of the 447 patent provides a "blanket of air", a substantially flat airflow across a field for entraining and collecting exhaled gases, generally from the mouth, using an air supply manifold and a matching scavenging manifold placed on either side of the face. No provision is made for supplying nitrous oxide to the patient.

As evidenced by the patents referenced above, nitrous oxide anesthesia is typically administered by way of mask over nose, and safety regulations say that mask must also collect (vacuum up) anesthesia gas that the patient exhales. These references generally show complicated masks that, in some cases protrude substantially from the patient's face and/or cover the patient's top lip. This obstructs dentist's view and access with tools, plus makes operating under the patient's top lip quite difficult.

Also, the prior art in the patents referenced above generally has the mask's in and out hoses going both ways around head and the two hoses have a slide clasp that is cinched up behind the head and/or the headrest to hold the mask on. Problems with this include interference with turning patients head, and the raised hose on cheek gets in way of dentist.

The "Safe Sedate" Dental Mask System, by Airgas Puritan Medical, is similar to some of the patent references above in that it is a dental mask fitting over (around) the patient's nose. The system relies on precise administration of the anesthetic gas to meet government compliance regulations. The system also evacuates gas that is not inhaled, but doesn't evacuate (scavenge) exhaled gas from the mouth.

The typical mask system, as shown in "Safe Sedate" and some of the patents, comprise a cup shaped element that fits over the patient's nose, somewhat like a smaller version of a traditional oxygen mask (which, albeit, usually encompasses both the nose and mouth). It is sometimes difficult to get a tight seal between the mask and the face, without exerting undue (uncomfortable) pressure on the mask. Additionally, it can be somewhat uncomfortable for the patient to wear.

Providing a system that delivers and scavenges anesthetic gas to a patient, without impairing access to the patient's mouth by a dentist, remains a challenge. What is needed is a more ergonomic design, addressing some of the shortcomings of the prior art, as noted above.

BRIEF DESCRIPTION (SUMMARY) OF THE INVENTION

It is a general object of the invention to provide improved apparatus for delivering anesthesia gas to a patient along with scavenging exhaled or leaked gas, particularly in the context of dentistry where unimpaired access to the patient's mouth is required.

According to the invention, generally, an apparatus for delivering and scavenging waste anesthetic gas (such as nitrous oxide) to a patient (such as a dental patient) comprises:

a gas delivery portion ("lower piece") comprising a nasal cannula which is generally an elongate tube extending (when mounted) across the patient's face, under the nose, with two tips (nostril tubes) for inserting into the patient's nostrils; and a gas scavenging portion ("upper piece") comprising an elongate tube (vacuum line) extending generally parallel to the cannula and arched over a lower portion of the patient's nose, with openings (such as slots) positioned towards the patient's mouth into which waste anesthesia gas exhaled by the patient can be drawn and exhausted.

The gas delivery portion is connected via a hose to a supply of anesthetic gas. Nipples for connecting the hoses are provided at both ends of the elongate gas delivery portion so that the gas delivery hose may be attached to either end of the gas delivery portion.

The gas scavenging portion is connected via a hose to a vacuum source. Nipples for connecting the hoses are provided at both ends of the elongate gas scavenging portion so that the gas scavenging hose may be attached to either end of the gas scavenging portion.

The two hoses may be different diameters to avoid connecting the gas delivery hose to the gas scavenging portion, and vice-versa.

Both hoses may be bundled (or held) together, parallel to one another. Conveniently, both hoses may be connected to a one end of the respective gas delivery and gas scavenging portions, so as to extend around only one side of the patient's head. The unused nipples at the other ends of the gas delivery and gas scavenging portions may be blocked off by a cap. This allows the dentist to position the hoses (tubing) on the opposite side of the patient's face from where he is working.

The gas delivery and gas scavenging hoses may pass under or over the patient's ear.

What can be considered to be "end portions" of the entire gas delivery portion may be integrally formed with end portions of the gas scavenging portion. And, a central portion of the entire gas delivery portion may be separate from the gas scavenging portion, and attachable thereto.

An adjustable strap extends from the two ends of the apparatus, such as from a back surface of the gas scavenging portion, and fits around the patient's head, approximately at the nape of the neck. The strap may be textile, or elastic, and may be disposable.

The apparatus is designed to sit flat against the patient's face with minimal coverage of the patient's top lip. Adult and child sizes may be provided. The apparatus sits far up enough on the face to allow for access to the upper gums. If the dentist does need to move the mask up a bit when working on the upper gums, the rigid top piece can move up a bit to make way, and the flexibility of the thin lower piece will allow the nostril tubes to stay in place while the flexible lower piece tubing can give way as the lip is raised for access to the upper gums.

The gas scavenging portion ("upper piece") may be formed from a very hard durometer but still slightly flexible silicone or autoclavable plastic, or co-injection molded with a metal or plastic structure inside of silicone, or a metal such as stainless steel, etc. It needs to be rigid enough to not collapse from suction, but flexible enough to be comfortable and have a bit of give when the dentist is working in the mouth, especially the upper areas. The upper piece is anticipated to be reusable, hence may be autoclavable (for sterilizing between usages on different patients).

The gas delivery portion ("lower piece") could also be made autoclavable, but preferably it is formed from a softer material, as it is anticipated to be disposable.

Other objects, features and advantages of the invention will become apparent in light of the following description thereof.

BRIEF DESCRIPTION OF THE DRAWINGS

Reference will be made in detail to preferred embodiments of the invention, examples of which are illustrated in the accompanying drawing figures. The figures are intended to be illustrative, not limiting. Although the invention is generally described in the context of these preferred embodiments, it should be understood that it is not intended to limit the spirit and scope of the invention to these particular embodiments.

Certain elements in selected ones of the drawings may be illustrated not-to-scale, for illustrative clarity. The cross-sectional views, if any, presented herein may be in the form of "slices", or "near-sighted" cross-sectional views, omitting certain background lines which would otherwise be visible in a true cross-sectional view, for illustrative clarity.

Elements of the figures can be numbered such that similar (including identical) elements may be referred to with similar numbers in a single drawing. For example, each of a plurality of elements collectively referred to as 199 may be referred to individually as 199a, 199b, 199c, etc. Or, related but modified elements may have the same number but are distinguished by primes. For example, 109, 109', and 109" are three different elements which are similar or related in some way, but have significant modifications. Such relationships, if any, between similar elements in the same or different figures will become apparent throughout the specification, including, if applicable, in the claims and abstract.

The structure, operation, and advantages of the present preferred embodiment of the invention will become further apparent upon consideration of the following description taken in conjunction with the accompanying drawings (FIGs), wherein.

DETAILED DESCRIPTION OF THE INVENTION

Generally, the invention relates to an apparatus for delivering an anesthetic gas to a patient, which the patient will inhale and exhale, and scavenging (removing) exhaled gas for disposal elsewhere. An example of anesthetic gas is nitrous oxide (which may be mixed with oxygen).

The gas discussed in the described embodiments is primarily anesthesia gas, but it should be understood that the gas scavenging function is intended to also include scavenging any gas-entrained or aerosol liquids, such as, for example, spattered or sprayed drill-cooling water mixed with saliva.

Generally, the anesthetic gas is delivered to the apparatus via a flexible "hose", or "tube". Likewise, the anesthetic gas which is collected from the apparatus is removed from the vicinity of the patient (and the doctor) via a flexible hose, or tube.

Generally, the apparatus is provided with "barbs" or "nipples" to which the hoses connect. A hose barb is typically a short cylindrical element, having an outside diameter approximately equal to the inside diameter of the hose which will be connected to it, and is often, but not necessarily provided with a few ridges extending around its circumference to cause an interference fit with the hose.

Generally, as used herein, the term "elongate member" means an element that has a length that is substantially greater than its width, and has two opposite ends.

Generally, as used herein, the term "end portion" means a portion of an element, such as an elongate member, extending from one end of the element towards the other end of the element.

Exemplary dimensions may be presented in the description below, and are intended to be illustrative, rather than limiting.

An embodiment of the invention will now be described in detail, with respect to FIGS. 1, 2, 3, 4 and 5.

Figure 1:
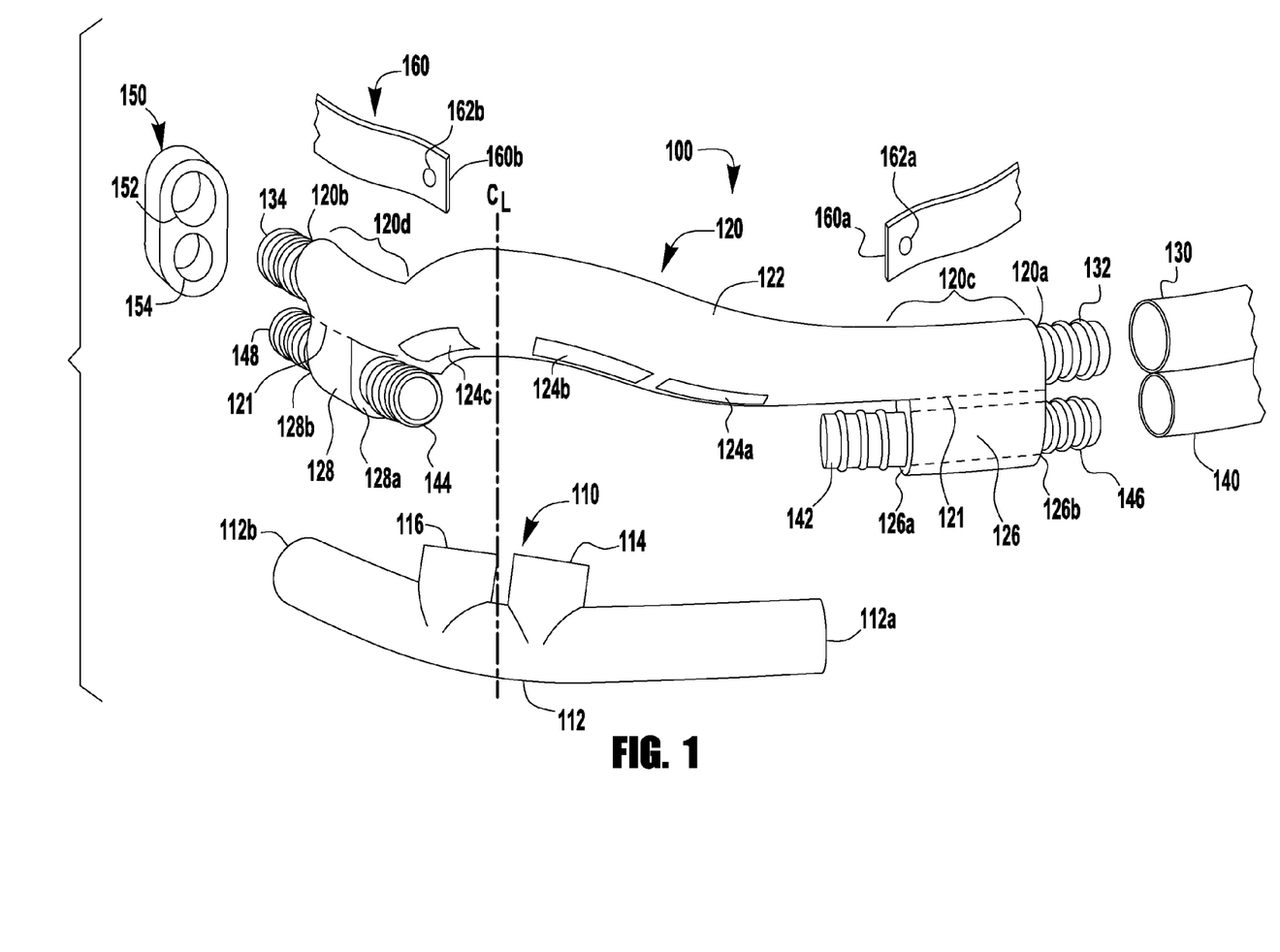
FIG. 1 is an exploded view of an embodiment of an apparatus for delivering anesthesia gas and scavenging gas (including the anesthesia gas) for a patient, according to the invention.

FIG. 1 illustrates an apparatus 100 for delivering and scavenging anesthetic gas (such as nitrous oxide) to a patient (such as a dental patient), with the major components shown separated from each other (exploded view). The apparatus 100 generally comprises a gas delivery portion ("lower piece") 110 and a gas scavenging portion ("upper piece") 120.

The gas delivery portion ("lower piece") 110 is a generally elongate member in the form of a tube 112 having two ends labeled 112a and 112b, a diameter of approximately 9 mm, and a length of approximately 76 mm. The tube 112 may be formed of a relatively flexible (rather than stiff) material, such as a thermoplastic elastomer, silicone or synthetic rubber, etc., and may be formed with a slight curve to it (as illustrated), since it is intended to lay substantially flat against a portion of a patient's face (see, for example, FIG. 5). The two ends 112a and 112b of the tube 112 are open, and will be connected to hose barbs (nipples 142, 144) on the upper piece 120, as described in greater detail hereinbelow.

Figure 5:
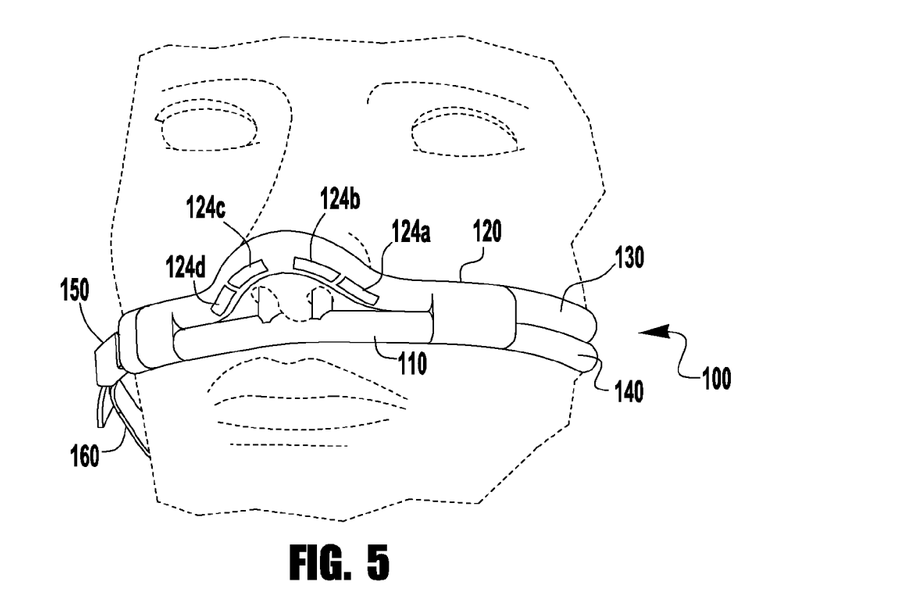
FIG. 5 is a view, looking upward, of the apparatus of FIG. 1 installed on a patient's head, according to the invention.

Two nostril tubes (or "prongs") 114, 116 extend radially from the tube at approximately a midpoint along the length of the lower piece 110, substantially parallel with one another and are sized, shaped and spaced from one another to fit comfortably (be inserted) within the nostril openings of a patient (see, for example, FIG. 5). For example, a nostril tube 114 has a diameter of 4-9 mm, and extends app. 8 mm from the tube 112, and is spaced 2 mm from the adjacent, substantially identically-sized nostril tube 116. The nose cannulas can vary in length, diameter, and distance between to fit children, women and men, etc. The nostril tubes 114, 116 are in fluid communication with the two ends 112a and 112b of the tube 112, so that anesthetic gas delivered to either end of the tube 112 will flow to both of the nostril tubes 114, 116. It is generally intended (anticipated) that the lower piece 110 will be disposable, rather than re-used among patients. The tube 112 and the upper piece 120 can be offered in different sizes to fit children, women and men. The tube 112 can be offered with different sized nose cannulas.

As described in greater detail hereinbelow, the lower piece 110 may be joined with (or mounted to) the upper piece 120, which has end portions for the lower piece 110, including hose barbs (barbs 146, 148) for receiving a hose (140) supplying the anesthetic gas.

In essence, the lower piece constitutes what is termed a "nasal cannula". The nasal cannula is a device, typically used in the hospital, in a pre-hospital setting, or at home to deliver, for example, supplemental oxygen to a patient or person in need of extra oxygen. This device consists of a plastic tube which fits behind the ears, and a set of two prongs which are placed in the nose or nares (nostrils). Oxygen flows from these prongs. In the present invention, anesthetic gas flows from the prongs, and the tubing for connecting the cannula is described hereinbelow.

The gas scavenging portion ("upper piece") 120 is a generally elongate member, having two ends 120a and 120b and, as will be evident, has an overall length which is greater than the length of the lower portion 110. The overall length of the upper piece 120 may be approximately 101 mm, exclusive of barbs.

The upper piece 120 comprises an elongate tube 122, extending from end-to-end of the upper piece. This tube 122 is for scavenging gas, and may have a diameter of approximately 11.6 mm. (The tube 122 may become rectangular or almost square on most of the nose, it may be about 11.6×11.7 mm so if it were a circular section, the diameter would be about 11.6 mm.) The length of the tube 122 is, by definition, the length of the upper piece 120. The tube 122 (and the entire upper piece 120) may be formed of a relatively stiff material, such as a relatively hard durometer silicone or autoclavable elastomer, a somewhat flexible autoclavable plastic, or a metal such as stainless steel and may be formed with a prominent curve to it (as illustrated), since it is intended to extend over a lower portion of a patient's nose (see, for example, FIGS. 2,3,4,5). For example, the tube 122 may be "bowed" (or "arched") approximately 10 mm to pass over the patient's nose. The intention is to arch only enough to pass over the lower portion of the patient's nose, thereby minimizing obstruction of view and hand/tool access by the dentist. Thus the upper piece 120 may be supplied in one or more sizes to accommodate, for example, small (e.g., children), medium and large noses.

The tube 122 is provided with a plurality of openings 124 (such as slots, or "inlet holes") that are provided on a lower portion of the tube 122, directed downward, so as to be positioned towards the patient's mouth. Generally designated "124", the purpose of the slots 124*a*, 124*b* and 124*c* (only three of four slots 124 are visible in the view of FIG. 1; all four slots 124*a*, 124*b*, 124*c*, 124*d* are visible in FIG. 5) is to scavenge waste anesthesia gas and/or aerosols and splatter which is exhaled or emitted by the patient, primarily from the patient's mouth (generally, with the nose substantially plugged up and mouth open, and anesthetized, the patient will be exhaling from their mouth), as well as anesthesia gas which may escape from the prongs 114, 116 without being inhaled by the patient.

The slots 124*a*, 124*b*, 124*c* may be generally rectangular, having a length of approximately 12 mm (aligned with the length of the tube 122), and a width of approximately 4 mm (the width of a slot is circumferential with respect to the tube 122). The three slots shown are merely exemplary. There may be more, or fewer slots. The openings may be several holes disposed along the length of the tube 122.

When connected to a vacuum source, the upper piece 120, and the openings 124 provided therein, preferably create a substantially laminar flow of air and gas over the chin and mouth area of the patient to scavenge waste anesthesia gas and/or "aerosols or splatter". Laminar flow, sometimes known as streamline flow, occurs when a fluid flows in parallel layers, with no disruption between the layers. In fluid dynamics, laminar flow is a flow regime characterized by high momentum diffusion, low momentum convection, and pressure and velocity independence from time. It is the opposite of turbulent flow. In nonscientific terms laminar flow is "smooth," while turbulent flow is "rough."

Attention is now directed to end portions 120*c* and 120*d* of the upper piece 120.

As best viewed on the right side (FIG. 1) of the upper piece 120, a first hose barb 132 extends from the right end 120*a* of the upper piece 120, and may be in fluid communication with the tube 122 (hence with the openings 124*a*, 124*b*, 124*c*). The hose barb 132 may have a length of approximately 10 mm, and an outside diameter of approximately 6.35 mm (slightly larger than hose barbs 146, 148) and may be provided with a few ridges extending around its circumference (exterior surface) to cause an interference (secure, yet removable) fit with a vacuum (exhaust) hose 130.

A second hose barb 134 (shown at an angle on the left), substantially identical to the first hose barb 132 extends from the opposite end 120*b* of the upper piece 120. As discussed in greater detail hereinbelow, the reason for two hose barbs 132 and 134 is to allow connection of the vacuum hose 130 to either side (end 120*a* or 120*b*) of the upper piece 120, depending on the dentist's preference. If there are two vacuum hoses, they could be connected to both sides of the upper piece 120.

The barbs 132 and 134 are associated with upper portions of the end portions 120*a* and 120*b* of the upper piece 120. Lower portions of the end portions 120*a* and 120*b* of the upper piece 120 are associated with the lower piece 110, and are discussed in greater detail hereinbelow.

Generally, the apparatus 100 is symmetrical (left and right) about a centerline (CL), which (when the apparatus is mounted on a patient's face) coincides with a line running down the patient's nose.

As mentioned hereinabove, the lower piece 110 may be joined with (or mounted to) the upper piece 120, which has end portions for the lower piece 110, including barbs for receiving a hose supplying the anesthetic gas. And, lower portions of the end portions 120*a* and 120*b* of the upper piece 120 are associated with the lower piece 110.

Attention is now directed to lower portions 126, 128 of the end portions 120*c* and 120*d* of the upper piece 120. A dashed line 121 indicates a "boundary" between upper and lower portions of the end portions 120*c* and 120*d*.

Generally, a lower portion 126 (representative of both lower portions 126, 128) extends from an end 120*a* of the upper piece 120 partially towards the opposite end 120*b* of the upper piece, such as 13 mm but could be less. It was mentioned above that the upper piece 120 may have an overall length (exclusive of barbs) of approximately 102 mm, and that the lower piece 110 may have length of approximately 76 mm. (Note that 76+13+13=102.)

The lower portion 126 extends approximately 9 mm below the upper piece, at the end portion 120*c*.

A first nipple 142 (similar to a hose barb, but not for receiving a hose), extends from an inner surface 126*a* of the lower portion 126. The purpose of the nipple 142 is to receive and fit securely (yet removably) in the end 112*a* of the tube 112. The nipple 142 may have a length of approximately 10 mm, and an outside diameter of approximately 6.35 mm. Note that this nipple is slightly larger than 146, and may be provided with a few ridges extending around its circumference (exterior surface) to cause an interference (secure, yet removable) fit with the tube 112.

A second nipple 144, substantially identical to the first nipple 142, extends from an inner surface 128*a* of the lower portion 128. The purpose of the nipple 144 is to receive and fit securely (yet removably) in the end 112*b* of the tube 112. The nipple 144 may have a length of approximately 10 mm, and an outside diameter of approximately 6.35 mm, and may be provided with a few ridges extending around its circumference (exterior surface) to cause an interference (secure, yet removable) fit with the tube 112.

The lower piece 110 is intended to be mounted to the upper piece 120, and is relatively flexible so that it can easily be bent manually (by hand) and its ends 112*a* and 112*b* inserted on the nipples 142 and 144, respectively, as well as easily removed after the dental procedure is completed. (In this regard, the open ends 112*a* and 112*b* of the tube 112, fitting over the nipples 142 and 144, respectively, constitute an example of "means" for positioning the lower piece 110 generally parallel and immediately adjacent to the upper piece 120, and removably securing it thereto. It is generally intended that the lower piece 110 is disposable, one-use only, for sanitary purposes.

It is within the scope of the invention that the two nipples 142 and 144 be dissimilar, such as a different diameter, or "keyed", and that the ends 112*a* and 112*b* of the tube 112 be correspondingly dissimilar so that the tube 112 can only be installed one way on the upper piece 110. However, it is believed that the angles made by the nipples 142 and 144 (they are generally not collinear, since the upper piece 120 is generally arcuate) will ensure correct installation. However, even with the angle, if the nipples 142 and 144 are substantially round, some rotational adjustment (albeit, only a few degrees) of the position of the lower piece 110 may be possible, to better fit the patient.

As best viewed on the right side (FIG. 1) of the upper piece 120, a first hose barb 146 extends from an outer surface 126*b* of the lower portion 126, and is in fluid communication with the nipple 142 (note dashed lines indicating an interior passageway). The hose barb 146 may have a length of approximately 10 mm, and an outside diameter of approximately 5.5 mm slightly smaller than 132, and may be provided with a few ridges extending around its circumference (exterior surface) to cause an interference (secure, yet removable) fit with an anesthesia gas supply hose 140.

On the left side of the upper piece 120, a second hose barb 148 extends from an outer surface 128b of the lower portion 128, and is in fluid communication with the nipple 144. The hose barb 148 may have a length of approximately 10 mm, and an outside diameter of approximately 5.5 mm, and may be provided with a few ridges extending around its circumference (exterior surface) to cause an interference (secure, yet removable) fit with the anesthesia gas supply hose 140.

The surface 126b corresponds to the end 120a of the upper piece 120. When the lower piece 110 is mounted to the upper piece 120, the surface 126b essentially constitutes an end of the lower piece 110.

Similarly, the surface 128b corresponds to the end 120b of the upper piece 120. When the lower piece 110 is mounted to the upper piece 120, the surface 128b essentially constitutes an opposite end of the lower piece 110.

The upper piece 120 is intended for multiple-use, and should be autoclavable. The upper piece 120 may also have some flexibility, to help conform to the patients face, but is generally intended to be relatively stiff in comparison with the lower piece 110.

Suitable materials for the lower piece 110 include injection molded thermoplastic elastomer, silicone, synthetic rubber, etc.

Suitable materials for the upper piece 120 include silicone of a stiff enough durometer to hold up to suction, autoclavable plastic that has some flex, stainless steel, etc. . . .

Two hoses have been mentioned above—a hose 130 connected to a vacuum source (not shown), and a hose 140 connected to a supply (not shown) of anesthesia gas. The vacuum hose barbs 132 and 134 may be a different size (diameter) than the gas hose barbs 134 and 148. Thus, the hoses 130 and 140 may have different diameters, corresponding to the different diameter barbs, to encourage correctly connecting the hoses—that is, connecting the vacuum hose 130 to either the barb 132 or 134, and connecting the gas supply hose 140 to either the barb 146 or 148. The two hoses 130, 140 can be molded in a single unit, or they can be separate but preferably attached to one another in any suitable manner, such as a band encircling the two hoses 130, 140.

Suitable materials for the hose 130 include silicone, synthetic rubber, autoclavable thermoplastic elastomer, etc.

Suitable materials for the hose 140 include silicone, synthetic rubber, autoclavable thermoplastic elastomer, etc.

The two tubes 130 and 140 may be integrated into one overall tube, as distinct passages in the overall tube.

In FIG. 1, the hoses 130, 140 are shown to be connected to the barbs 132, 146 on the right (as viewed in the drawing, which would be "left" as mounted on the patient's face) end 120a of the upper piece 120 (which is the right side of the overall apparatus 100). This is so the doctor can position both of the hoses 130, 140 on the same—in this example, left—side of the patients face, thereby eliminating interference with the dentist's hands as he works from the other side of the patient's face.

In order that the apparatus 100 may function properly, the "unused" barbs—in this example, the barbs 134 and 138 on the opposite (left, as viewed) end 120b of the apparatus 100 must be closed off, and made substantially "airtight", so that anesthesia gas does not flow into the operating environment, and so that the vacuum is not compromised.

An end cap 150 is provided for sealing (closing) a set (a "set" being, for example, 134/148) of unused barbs. The end cap is suitably formed of a resilient material, such as rubber, silicone or elastomer, and may have two holes 152, 154 extending into (but not through) the body of the end cap from a surface thereof. The hole 152 has a diameter substantially equal to the inside diameter of the vacuum hose 130, and the hole 154 has a diameter substantially equal to the inside diameter of the supply hose 140.

Suitable materials for the end cap 150 include silicone, synthetic rubber, autoclavable thermoplastic elastomer, etc. . . .

If the dentist prefers, he can connect the hoses 130, 140 to the barbs 134, 148 on the left side of the apparatus 100, and close off the barbs 132, 146 on the right side of the apparatus 100 using the end cap 150. The end cap 150 may be attached with a flexible cord to a portion of the apparatus 100, so that it does not become misplaced and lost.

Figure 6:
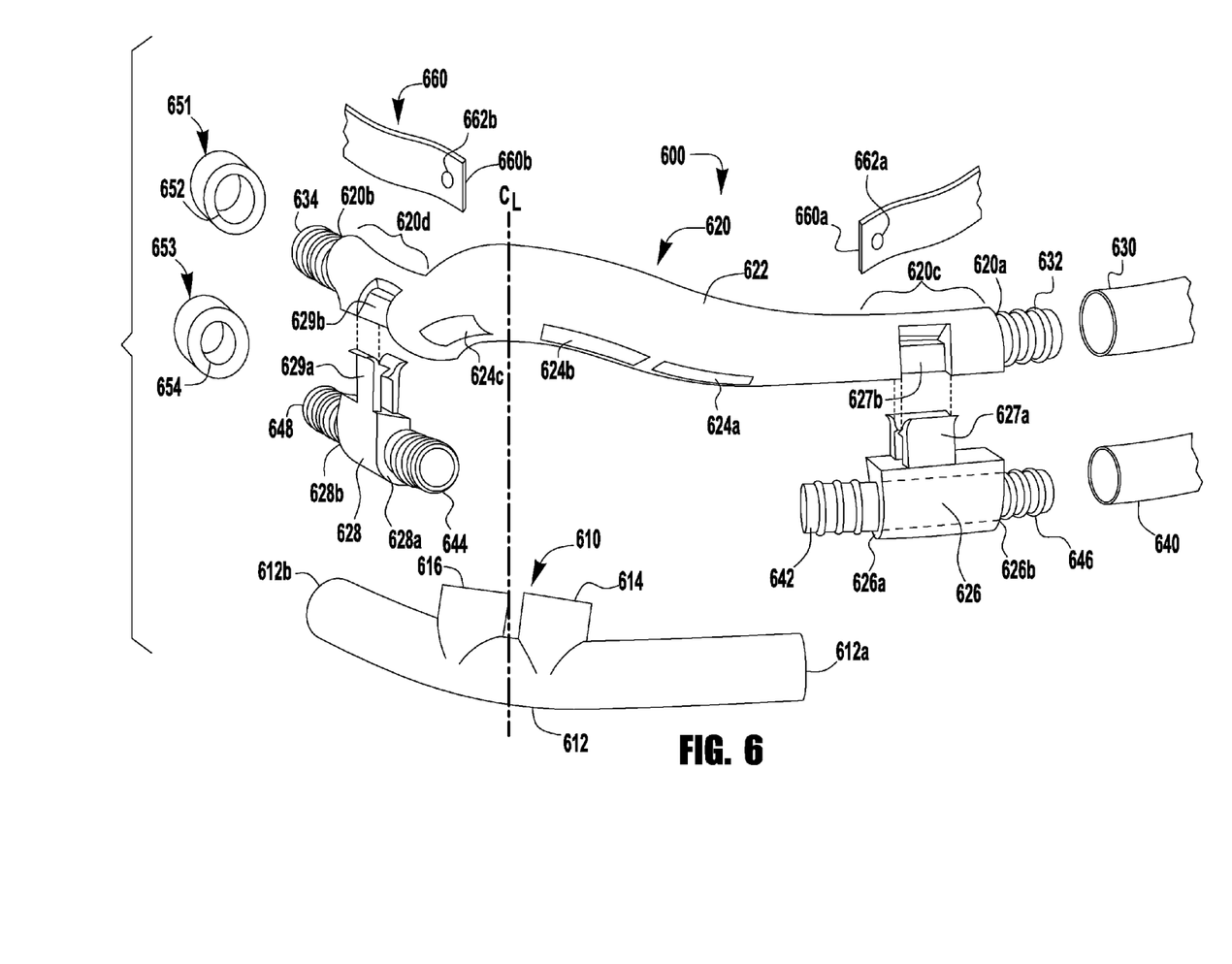
FIG. 6 is an exploded view of an alternate embodiment of an apparatus for delivering anesthesia gas and scavenging gas (including the anesthesia gas), according to the invention.

As mentioned above, it is generally preferred that the two hoses 130 and 140 be somehow "bundled together" for simultaneous connection to the associated pair of barbs (e.g., 132, 146) on a given side (end) of the apparatus 100. Similarly, it is generally preferred that the end cap 150 be capable of simultaneously closing off the unused pair of barbs (e.g., 134, 148). It can be observed that the pair of hose barbs 132, 146 at one end of the apparatus 100 is substantially identical (size, shape, spacing) to the pair of hose barbs 134, 148 at the opposite end of the apparatus 100 to facilitate the hoses 130, 140 and end cap 150 being selectively connected to either side of the apparatus 100. Of course, two separated individual hose barb caps (e.g., 651, 653 as shown in FIG. 6) could be used rather than the single end cap 150 to seal off selected individual barbs.

A strap 160 is provided for securing the apparatus 100 to the patient's face. In FIG. 1, only the ends 160a and 160b of the strap are shown. The end 160a attaches, in any suitable manner, behind the end portion 120c of the upper piece 120. The end 160b attaches, in any suitable manner, behind the end portion 120d of the upper piece 120. Any suitable means can be used for removably, or even permanently, securing the strap ends 160a, 160b to the end portions 120c, 120d, respectively, of the upper piece 120. For example, a one portion of a clasp, catch, or other fastening device can be provided on end portions of the strap 160, as illustrated by circles 162a and 162b, to be engaged with corresponding mating portions of the clasp, catch, or other fastening device provided on the anterior (not visible) surface of the end portions 120c and 120d, respectively, of the upper piece 120. Since the strap 160 is disposed on the inner, face side of the apparatus 110, the end portions 120c and 120d may be provided with recesses (not shown) for receiving the ends 160a and 160b of the strap 160, while presenting a generally smooth surface which will be against the patient's face. For example, the fastening devices 162a, 162b could be the fastening means of embedding the strap ends 160a, 160b in the material of the upper piece 120.

Figure 2:
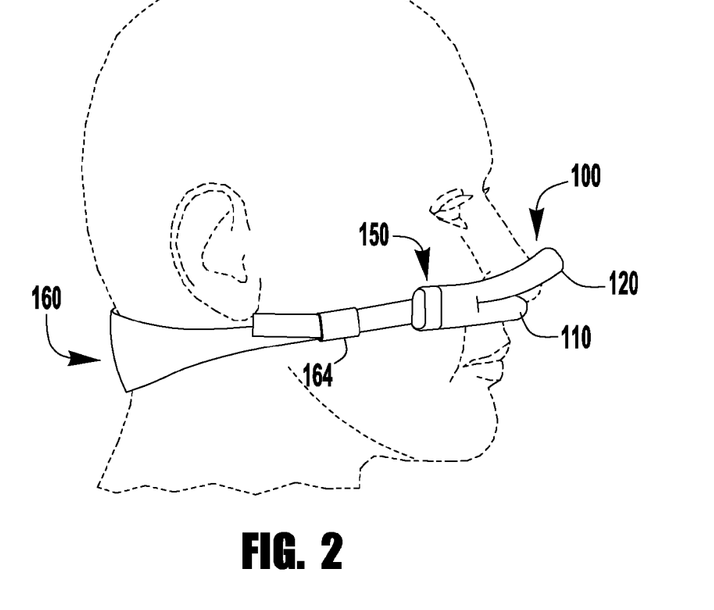
FIG. 2 is a side view of the apparatus of FIG. 1, installed on a patient's head, according to the invention.

Any suitable means may be provided for adjusting the length of the strap 160, such as the buckle 164 shown in FIG. 2. Strap 160 and buckle 164 could be silicone, autoclavable plastic and/or metal, and could be constructed like the strap on a scuba mask. Alternatively, the strap 160 could be an elastic band such as is used to hold on surgical face masks. However it is implemented, the strap 160 is preferably a thin band that lies relatively flat on the cheek such that it minimizes obstruction of the dentist's hands on the side opposite to the side with hoses.

Suitable materials for the strap 160 include silicone, autoclavable thermoplastic elastomer, elastic fabric, etc., and the strap 160 may be a little wider where it sits on (engages) the back of the patient's neck, as best viewed in FIG. 2.

An example of an autoclavable TPE (thermoplastic elastomer) is FlexiPrene™. Offered as extruded tubing or injection molded components, FlexiPrene™ pharmaceutical grade TPE may be heat sealed, welded, or sterilized by autoclave, gamma radiation, or EtO. Injection moldable material allows for leak-free connections and eliminates entrapment issues in manifolds and assemblies. Free of silicone oils and animal-derived ingredients, flexible tubing offers resistance to kinking and comes in 3/32-1½ in. OD sizes.

FIG. 1, discussed extensively above, is an exploded view of the apparatus 100.

FIG. 2 is a side view of the apparatus 100, installed on a patient's head. In this view, the left side of the apparatus (from the perspective of FIG. 1) is shown on the right side (from the patient's perspective) of the head. With the end cap 150 on this side, only the strap 160 and the buckle 164 lie on the patient's face, both of which are intentionally as thin and unobtrusive as possible, therefore presenting a substantially open field for the dentist's hands and tools on that side of the face.

Figure 3:
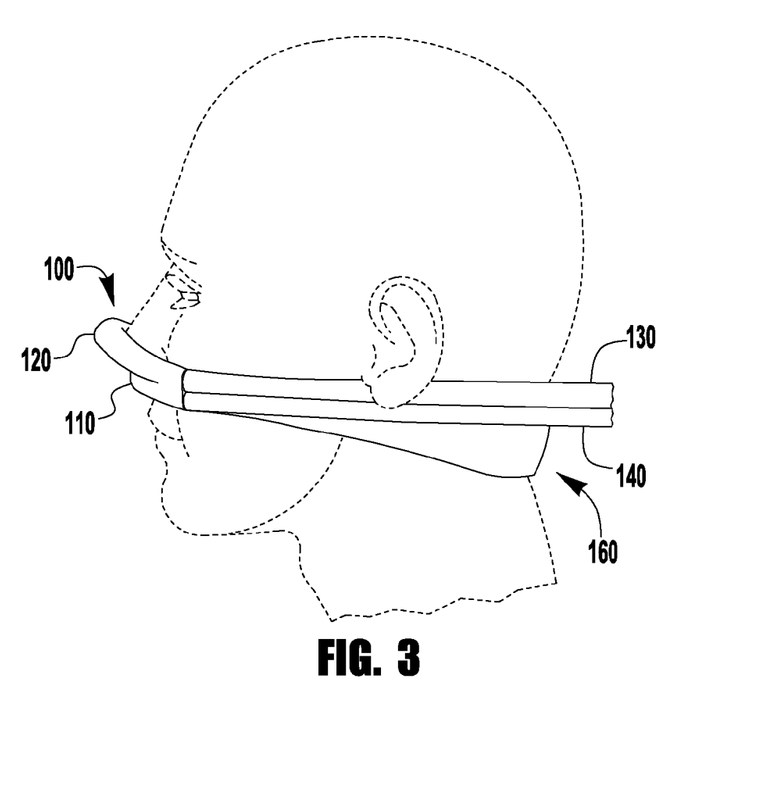
FIG. 3 is an opposite side view of the apparatus of FIG. 1, installed on a patient's head, according to the invention.

FIG. 3 is a side view of the apparatus 100, installed on a patient's head. In this view, the right side of the apparatus (from the perspective of FIG. 1) is shown on the left side (from the patient's perspective) of the head. The two hoses 130, 140 are both on this side which is the opposite of the side used by the dentist.

Figure 4:
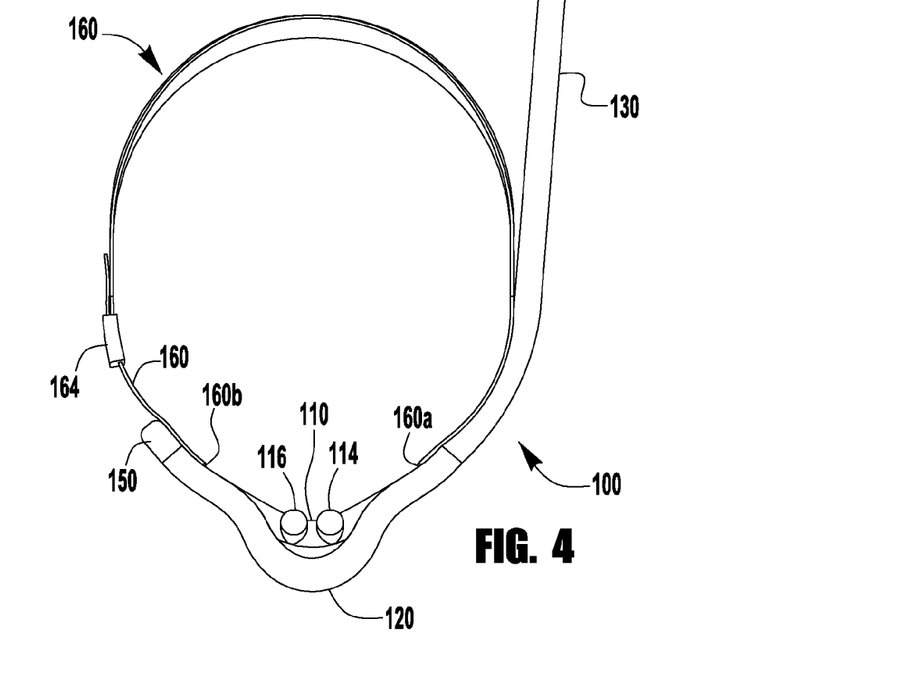
FIG. 4 is a view, looking down on a patient's head, with the apparatus of FIG. 1 installed, according to the invention.

FIG. 4 is a view, looking down on a patient's head (not shown), with the apparatus 100 fully assembled and configured as if installed on a patient's head. In this view, the position of the strap ends 160*a*, 160*b* behind the end portions of the upper piece 120 is apparent. Here, as mentioned hereinabove, the upper piece 120 (the tube 122) may be formed with a prominent curve to it (as illustrated), since it is intended to extend over a lower portion of a patient's nose. The lower piece 110 is much closer to the patient's face (upper lip) so that the nostril tubes 114, 116 will fit up into the patient's nostrils.

FIG. 5 is a view, looking upward, of the apparatus 100, installed on a patient's head. In this view, four openings (holes) 124*a*, 124*b*, 124*c*, 124*d* in the underside of the upper piece 120 are visible.

There has thus been described an embodiment of an apparatus for delivering and scavenging gases, especially anesthesia gas. It should be appreciated that the apparatus is also suitable for scavenging other "gases", including aerosols, splatter, etc. emanating from the nose and mouth area of a patient.

In the embodiment described hereinabove, with respect to FIGS. 1-5, end portions 126, 128 of the gas delivery apparatus (the lower piece 110) are integrally formed with end portions 120*c*, 120*d* of the gas scavenging apparatus (the upper piece 120). Thus, the upper and lower pieces are not entirely separate from one another. It is within the scope of the invention that the upper and lower pieces be entirely separate (separately formed) from one another, in which case the lower piece 110 would be longer, and would have its own barbs 146, 148, and a means for connecting the lower piece 110 to the upper piece 120 would also be provided. For example, the lower piece 110 could "snap fit" to the upper piece 120. Or, a band could connect the upper and lower pieces. Or, instead of the portions 126 and 128 extending down from the upper piece 120, generally U-shaped clips/clamps could extend downward to "capture" end portions of the lower piece 110, for example. Or, U-shaped clips could extend upward from end portions (126, 128) of the lower piece (110) to releasably engage the upper piece (120). However, it is believed that the embodiment described hereinabove, with the lower end portions 126, 128 of the delivery apparatus lower piece 110 being integrally formed with end portions 120*c*, 120*d* of the scavenging apparatus upper piece 120, offers superior performance by avoiding the lower portion becoming disassociated from the upper portion during the procedure. In all of these examples, the lower piece 110 is somehow positioned generally parallel and immediately adjacent to the upper piece 120, for example along the imaginary line 121 illustrated in FIG. 1.

FIG. 6 illustrates an alternate embodiment of an apparatus for delivering anesthesia gas and for scavenging gas (including the anesthesia gas), according to the invention. This embodiment is nearly identical to the embodiment described with respect to FIGS. 1-5, except that (as mentioned in the previous paragraph) the upper and lower pieces are entirely separate (separately formed) from one another, the lower piece is longer and has its own barbs, and means for connecting the lower piece to the upper piece is provided. Generally, the means for connecting the lower piece to the upper piece is illustrated as U-shaped clips extending upward from end portions of the lower piece to releasably engage the upper piece. It should be understood that the illustrated connection means is but one of many possible connection means within the scope of the present invention, some other examples of which are mentioned above, none of which are intended to be limiting of scope. The lower piece, including its end portions can be removably attached to upper portion such that either piece could be used independently of the other. In particular, the upper piece by itself could be used to evacuate aerosols and splatter even when gaseous anesthesia is not being administered. With an attached strap and a vacuum hose on one side, the same advantage of minimal obstruction on one side of the face could be achieved. Alternatively, using two vacuum hoses, one on each side, would greatly increase the scavenging effectiveness of the upper piece.

Another variation which will be described with respect to FIG. 6 is that the end cap can be split into separate round caps. Separate round caps could also be used with the original (FIG. 1) apparatus 100 if it is desired to add a second vacuum line 130 to the other side of the apparatus to boost exhaust, in which case there would be (for example) a double hose on the right (as viewed), but on the left the top barb 134 would be connected to an extra tube (like 130) and the bottom barb 148 would be capped off by a single cap.

FIG. 6 illustrates an apparatus 600 (compare 100) for delivering and scavenging anesthetic gas (such as nitrous oxide) to a patient (such as a dental patient), with the major components shown separated from each other (exploded view). The apparatus 600 generally comprises a gas delivery portion ("lower piece") 610 and a gas scavenging portion ("upper piece") 620.

As will become evident, nearly all of the elements of the apparatus 600 are substantially identical to corresponding elements of the apparatus 600, and the reference numerals for such substantially identical elements being simply incremented by +500 are representative of this. (For example, the top piece 120 of FIG. 1 "becomes" the top piece 620 of FIG. 6.) Relevant materials, dimensions and shapes may also be substantially the same, and therefore need not be further discussed.

The upper piece 620 comprises an elongate tube 622, and has two ends 620*a* and 620*b*, and is for scavenging gas, including anesthesia gas, or other "waste" gas. The tube 622 is provided with a plurality of openings/slots 624*a*, 624*b*, 624*d* (only three of four slots are visible in this view) that are provided on a lower portion of the tube 622, directed downward, so as to be positioned towards the patient's mouth.

On the right side (as viewed) of the upper piece 620, a first hose barb 632 extends from the right end 620a of the upper piece 620, and may be in fluid communication with the tube 622. A second hose barb 634 extends from the opposite end 620b of the upper piece 620. If there are two vacuum hoses, they could be connected to both sides of the upper piece 620.

The lower piece 610 comprises a generally elongate member in the form of a tube 612 having two ends labeled 612a and 612b. Two nostril tubes 614, 616 extend radially from the tube at approximately a midpoint along the length of the lower piece 610.

Notice in FIG. 6 that the upper piece 620 does not have lower portions (126, 128). Recall that (in FIG. 1) although the lower portions (126, 128) were formed with the upper piece (120), they were functionally associated with the lower piece (110). In this embodiment, the analog of the lower portions (126, 128) is end portions 626 and 628, which are separate from the upper piece 620.

A first nipple 642, extends from an inner surface 626a of the end portion 626. The purpose of the nipple 642 is to receive and fit securely (yet removably) in the end 612a of the tube 612.

A second nipple 644, substantially identical to the first nipple 642, extends from an inner surface 628a of the end portion 628. The purpose of the nipple 644 is to receive and fit securely (yet removably) in the end 612b of the tube 612.

A first hose barb 646 extends from an outer surface 626b of the end portion 626, and is in fluid communication with the nipple 642.

A second hose barb 648 extends from an outer surface 628b of the end portion 628, and is in fluid communication with the nipple 644.

In the previously-described embodiment of FIGS. 1-5, the surfaces 126b and 128b were described as "essentially constituting" ends of the lower piece 110. In this embodiment (FIG. 6), the end portions 626 and 628 are not only functionally associated with the lower piece 610, but are removable parts of the lower piece 610.

A clip 627a is provided on an upper surface of the end portion 626 of the lower piece 620, and a corresponding indented profile 627b is provided on a lower surface of the end portion 620c of the upper piece 620. Together, the clip 627a and the profile 627b constitute an example of a means for connecting the lower piece 610 to the upper piece 620.

A clip 629a is provided on an upper surface of the end portion 628 of the lower piece 620, and a corresponding indented profile 629b is provided on a lower surface of the end portion 620d of the upper piece 620. Together, the clip 629a and the profile 629b constitute an example of a means for connecting the lower piece 610 to the upper piece 620.

The clips 627a, 629a and associated profiles 627b, 629b also constitute an example of means for positioning the lower piece generally parallel and immediately adjacent to the upper piece, and removably securing it thereto.

A strap 660 is shown. A one portion of a clasp, catch, or other fastening device can be provided on end portions of the strap 660, as illustrated by circles 662a and 662b, to be engaged with corresponding mating portions of the clasp, catch, or other fastening device provided on the anterior (not visible) surface of the end portions 620c and 620d, respectively, of the upper piece 620.

A hose 630 connected to a vacuum source may be attached to either the barb 632 or the barb 634, and the other (unused) barb may be plugged by a cap 651 having a hole 652. Or, two vacuum hoses may be attached to both barbs 632 and 634, in which case no cap 651 is required.

A hose 640 connected to a gas supply source may be attached to either the barb 646 or the barb 648, and the other (unused) barb may be plugged by a cap 653 having a hole 654. Or, two vacuum hoses may be attached to both barbs 646 and 648, in which case no cap 653 is required.

It is within the scope of the invention that additional mechanical features be incorporated into the design to make the apparatus 100 fit more securely or comfortably to the patient's face—for example, an arched element extending from the upper piece 120 across the patient's nose bridge. However, it is believed that the embodiment, as described hereinabove, is entirely adequate for the intended purpose(s).

Although the invention has been illustrated and described in detail in the drawings and foregoing description, the same is to be considered as illustrative and not restrictive in character—it being understood that only preferred embodiments have been shown and described, and that all changes and modifications that come within the spirit of the invention are desired to be protected. Undoubtedly, many other "variations" on the "themes" set forth hereinabove will occur to one having ordinary skill in the art to which the present invention most nearly pertains, and such variations are intended to be within the scope of the invention, as disclosed herein.

What is claimed is:

1. Apparatus for delivering and/or scavenging gas in the nose/mouth area of a patient, the apparatus comprising:
    an upper piece comprising an elongate tube formed with a prominent curve so as to extend over a lower portion of the patient's nose, and having a plurality of openings disposed on a lower surface thereof, so as to be directed downward towards the patient's mouth, for scavenging gas;
    a lower piece comprising an elongate tube forming a nose cannula having nostril tubes for inserting in the patient's nostrils, for delivering anesthesia gas to the patient;
    a first hose barb extending from one end of the upper piece;
    a second hose barb, substantially identical to the first hose barb, extending from an opposite end of the upper piece;
    a third hose barb extending from a first end portion of the lower piece;
    a fourth hose barb, substantially identical to the third hose barb, extending from an opposite end portion of the lower piece;
    wherein the first and third hose barbs are disposed on one side of the apparatus and the second and fourth hose barbs are disposed on an opposite side of the apparatus; and
    an end cap for sealing a one of the first and second hose barbs when a first hose is attached to the other of the first and second hose barbs, and for sealing a corresponding one of the third and fourth hose barbs when a hose is attached to the other of the third and fourth hose barbs.

2. The apparatus of claim 1, further comprising:
    a first hose extending from an end of the upper piece; and
    a second hose extending from a corresponding end of the lower piece, so that the first and second hoses may both go around a same side of the patient's face.

3. The apparatus of claim 1, further comprising:
    means for connecting the lower piece to the upper piece.

4. The apparatus of claim 3, wherein the means for connecting the lower piece to the upper piece comprises:
    a first clip provided on an upper surface of a first end portion of the lower piece, and a corresponding first indented profile provided on a lower surface of a first end portion of the upper piece; and a second clip provided on an upper surface of a second end portion of the lower piece, and a corresponding second indented profile provided on a lower surface of a second end portion of the upper piece.

5. The apparatus of claim 3, wherein the means for connecting the lower piece to the upper piece constitutes means for positioning the lower piece generally parallel and immediately adjacent to the upper piece, and removably securing it thereto.

6. The apparatus of claim 1, wherein:
the third and fourth hose barbs have a different diameter than the first and second hose barbs.

7. The apparatus of claim 1, further comprising:
means for positioning the lower piece generally parallel and immediately adjacent to the upper piece, and removably securing it thereto.

8. The apparatus of claim 7, wherein the means for positioning comprises:
a first nipple extending from a first end portion of the lower piece;
a second nipple, substantially identical to the first nipple, extending from an opposite end portion of the lower piece; and
open ends of the elongate tube engaging the first and second nipple, respectively.

9. The apparatus of claim 8, wherein:
the first and second nipples have ridges to ensure a secure, yet removable fit with the tube.

10. The apparatus of claim 1, wherein the lower piece is disposable, one-use only, for sanitary purposes.

11. The apparatus of claim 1, wherein the lower piece is formed of a material selected from the group consisting of injection molded thermoplastic elastomer, silicone and synthetic rubber.

12. The apparatus of claim 1, wherein:
the end cap comprises a first piece for sealing the one of the first and second hose barbs, and a second piece, separated from the first piece, for sealing the one of the third and fourth hose barbs.

13. The apparatus of claim 12, wherein:
the first and second barbs are provided with ridges to ensure a secure, yet removable fit with a hose.

14. The apparatus of claim 1, further comprising:
a strap having two ends; and
means for removably securing the strap to end portions of the upper piece.

15. The apparatus of claim 14, further comprising:
means for adjusting a length of the strap.

16. The apparatus of claim 14, wherein the strap is formed of a material selected from the group consisting of silicone, autoclavable thermoplastic elastomer and elastic fabric.

17. The apparatus of claim 1, wherein the upper piece is formed of a material selected from the group consisting of silicone of a stiff enough durometer to hold up to suction, autoclavable plastic that has some flex, and stainless steel.

* * * * *